(12) United States Patent
Kapiamba et al.

(10) Patent No.: US 8,349,987 B2
(45) Date of Patent: Jan. 8, 2013

(54) ADHESIVE FORMULATIONS

(75) Inventors: Mbiya Kapiamba, Cromwell, CT (US);
Jack Kennedy, Guilford, CT (US);
Roland Ostapoff, East Haven, CT (US)

(73) Assignee: Covidien LP, Mansfield, MA (US)

( * ) Notice: Subject to any disclaimer, the term of this patent is extended or adjusted under 35 U.S.C. 154(b) by 300 days.

(21) Appl. No.: 12/698,216

(22) Filed: Feb. 2, 2010

(65) Prior Publication Data

US 2010/0209380 A1    Aug. 19, 2010

Related U.S. Application Data

(60) Provisional application No. 61/153,714, filed on Feb. 19, 2009.

(51) Int. Cl.
| C08G 18/00 | (2006.01) |
| C08G 18/08 | (2006.01) |
| C08G 63/00 | (2006.01) |
| C08G 73/00 | (2006.01) |
| A61K 31/74 | (2006.01) |
| C08F 283/04 | (2006.01) |
| C09J 4/00 | (2006.01) |
| C09J 101/00 | (2006.01) |
| C09J 201/00 | (2006.01) |

(52) U.S. Cl. ............. 528/44; 528/52; 528/53; 528/80; 528/81; 424/78.06; 156/331.4; 525/440.01; 525/454

(58) Field of Classification Search ............. 424/78.06; 528/44, 52, 53, 80, 81; 156/331.4; 525/440.01, 525/454
See application file for complete search history.

(56) References Cited

U.S. PATENT DOCUMENTS

| 3,743,665 A * | 7/1973 | Naito et al. .................. 560/332 |
| 4,061,662 A | 12/1977 | Marans et al. |
| 4,169,175 A | 9/1979 | Marans et al. |
| 4,359,049 A | 11/1982 | Redl et al. |
| 4,361,055 A | 11/1982 | Kinson |
| 4,393,166 A | 7/1983 | Reischl et al. |
| 4,874,368 A | 10/1989 | Miller et al. |
| 4,978,336 A | 12/1990 | Capozzi et al. |
| 4,979,942 A | 12/1990 | Wolf et al. |
| 5,218,058 A | 6/1993 | Zeitler et al. |
| 5,278,275 A | 1/1994 | Yatsuka et al. |
| 5,368,563 A | 11/1994 | Lonneman et al. |
| 6,329,440 B2 | 12/2001 | Scherzer et al. |
| 6,527,749 B1 | 3/2003 | Roby et al. |
| 6,994,792 B2 | 2/2006 | Schlegel |
| 7,084,099 B2 | 8/2006 | Radomyselski et al. |
| 2004/0198900 A1 | 10/2004 | Madaj |
| 2005/0277734 A1 | 12/2005 | Kime |
| 2006/0128927 A1 | 6/2006 | Gurtler et al. |
| 2006/0280720 A1 * | 12/2006 | Fitz et al. .................. 424/78.27 |
| 2007/0276121 A1 | 11/2007 | Westergom et al. |

FOREIGN PATENT DOCUMENTS

| EP | 1 719 530 | 11/2006 |
| EP | 2002850 A2 | 12/2008 |
| GB | 985144 | 3/1965 |
| WO | WO 01/16210 A1 | 3/2001 |
| WO | WO 2007/067623 A2 | 6/2007 |

OTHER PUBLICATIONS

European Search Report from EP 08253647.5 dated Mar. 6, 2009.
European Search Report for EP 10250290.3-2102 date of completion is Jul. 23, 2010 (6 pages).

* cited by examiner

*Primary Examiner* — Abigail Fisher

(57) ABSTRACT

The disclosure relates to biocompatible components useful for forming compositions for use as medical/surgical synthetic adhesives and sealants. Biocompatible components of the present disclosure may include a polymeric polyol core, which may be treated with a nitroaryl compound to form a nitro ester. The resulting nitro ester groups may be reduced to form amino groups which, in turn, may be treated to form isocyanate groups. The resulting isocyanate may then be reacted with a second component to form adhesive and/or sealant compositions.

10 Claims, No Drawings

ADHESIVE FORMULATIONS

CROSS-REFERENCE TO RELATED APPLICATIONS

This application claims priority to U.S. Provisional Patent Application Ser. No. 61/153,714 filed on Feb. 19, 2009, the disclosure of which is hereby incorporated by reference in its entirety.

TECHNICAL FIELD

The present disclosure relates to adhesives and sealants formed from synthetic components for medical and surgical use with animal tissues in vivo.

BACKGROUND OF RELATED ART

In recent years there has developed an increased interest in replacing or augmenting sutures with adhesive bonds. The reasons for this increased interest include: (1) the potential speed with which repair might be accomplished; (2) the ability of a bonding substance to effect complete closure, thus preventing seepage of fluids; and (3) the possibility of forming a bond without excessive deformation of tissue or additional injury to tissue.

Studies in this area, however, have revealed that in order for surgical adhesives to be accepted by surgeons, they should possess various properties. For example, they should exhibit high initial tack and an ability to bond rapidly to living tissue; the strength of the bond should be sufficiently high to cause tissue failure before bond failure; the adhesive should form a bridge, typically a permeable flexible bridge; and the adhesive bridge and/or its metabolic products should not cause local histotoxic or carcinogenic effects.

Several materials useful as tissue adhesives or tissue sealants are currently available. One type of adhesive that is currently available is a cyanoacrylate adhesive. However, there is the possibility that a cyanoacrylate adhesive can degrade to generate undesirable by-products such as formaldehyde. Another disadvantage with cyanoacrylate adhesives is that they can have a high elastic modulus which can limit their usefulness.

Another type of tissue sealant that is currently available utilizes components derived from bovine and/or human sources. For example, fibrin sealants are available. However, as with any natural material, variability in the material is frequently observed and, because the sealant is derived from natural proteins, there may be viral transmission concerns.

It would be desirable to provide a surgical adhesive or sealant that is fully synthetic and therefore highly consistent in its properties without the concern of viral transmission. Such a composition should be flexible and biocompatible and should be suitable for use as an adhesive or sealant.

SUMMARY

Biocompatible compositions are provided which may be utilized, in embodiments, as tissue adhesives and/or tissue sealants. In embodiments, a biocompatible composition of the present disclosure may include a component of the following formula:

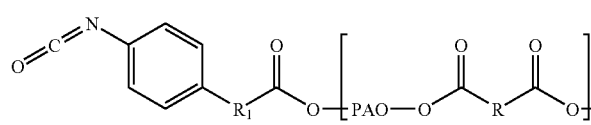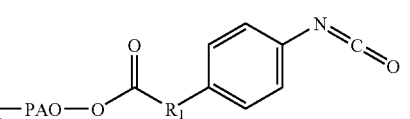

(I)

wherein R can be alkyl groups, cycloalkyl groups, alkenyl groups, alkynyl groups, alkylene groups, cycloalkylene groups, alkenylene groups, alkynylene groups, aromatic groups, heteroaromatic groups, heterocyclic groups, and combinations thereof, and n is a whole number from about 1 to about 5, in embodiments from about 2 to about 3;

$R_1$ can be the same or different at each location and can be $CH_2$, alkyl, $OCH_2$, $SCH_2$, $NHCH_2$, O-alkyl, S-alkyl, NH-alkyl, O-aryl, NH-aryl, and combinations thereof; and PAO is a polyalkylene oxide having a molecular weight of from about 200 to about 4000.

Processes for making these biocompatible compositions are also provided. In embodiments, a process of the present disclosure may include contacting a polyol with a nitroaryl carboxylic derivative to form a compound such as nitroaryl esters and/or nitroaryl ethers; contacting the nitroaryl esters and/or nitroaryl ethers with a reducing agent such as palladium with hydrogen, palladium with ammonium formate, platinum oxide with hydrogen, nickel with hydrogen, tin(II) chloride, iron with acetic acid, aluminum with ammonium chloride, borane, sodium dithionite, hydrazine, and combinations thereof, to form a second compound including amino esters and amino ethers; converting the amino ester or the amino ether to a corresponding isocyanate ester or isocyanate ether by contact with a reactant such as phosgene, diphosgene, triphosgene, 4-nitrophenyl chloroformate, and combinations thereof, optionally in the presence of a base, optionally in the presence of an aprotic solvent; and recovering the isocyanate ester or isocyanate ether.

Methods for using the compositions of the present disclosure as tissue adhesives and/or tissue sealants are also provided. In embodiments, such methods may include closing wounds, sealing leaks in animal tissue, adhering medical devices to tissue, combinations thereof, and the like.

DETAILED DESCRIPTION

The present disclosure relates to biocompatible compositions for use as tissue adhesives or sealants, which are non-immunogenic and biodegradable. The biocompatible compositions can be employed to approximate tissue edges, adhere medical devices (e.g. implants) to tissue, seal air/fluid leaks in tissues, and for tissue augmentation such as sealing or filling voids or defects in tissue. Thus, as used herein, an "adhesive" is understood to include a composition which adheres one thing to another, such as tissue edges to each other, or a device, such as an implant, to tissue; and a "sealant" is understood to include a composition which is applied to tissue and utilized to seal air/fluid leaks in tissue or seal or fill small voids or defects in tissue. However, an adhesive composition herein may be used as a sealant, and a sealant composition may be used as an adhesive.

The biocompatible compositions can be applied to living tissue and/or flesh of animals, including humans. While certain distinctions may be drawn between the usage of the terms "flesh" and "tissue" within the scientific community, the terms are used interchangeably herein as referring to a general substrate upon which those skilled in the art would understand the present composition to be utilized within the medical field for the treatment of patients. As used herein, "tissue" may include, but is not limited to, skin, bone, neuron, axon, cartilage, blood vessel, cornea, muscle, fascia, brain, prostate, breast, endometrium, lung, pancreas, small intestine, blood, liver, testes, ovaries, cervix, colon, stomach, esophagus, spleen, lymph node, bone marrow, kidney, peripheral blood, embryonic tissue, and/or ascite tissue.

In accordance with the present disclosure, a biocompatible component is provided which includes a polymeric core. Suitable cores which may be utilized include, but are not limited to, polymeric polyols, including polymeric diols such as polyether diols, polyester diols, polyester-urethane diols, combinations thereof, and the like. Other polymeric polyols which may be utilized to form a polymeric core in accordance with the present disclosure include, but are not limited to, block copolymers including branched chain ethoxylated alcohols; alkoxylated alcohols such as NEODOL® which is sold commercially by Shell Chemical Company; polyvinyl alcohols; polyhydric alcohols; carboxylic acid esters of polyhydric alcohols; polyglycols; polylactone polyols; combinations thereof, and the like.

In some embodiments, suitable polyols for use as the polymeric polyol include polyether-based polyols such as those based upon polyalkylene oxides including, but not limited to, polyethylene glycols ("PEG"), polypropylene glycols ("PPG"), polyethylene oxides ("PEO"), polypropylene oxides ("PPO"), polyethylene glycols with lactide linkages, polypropylene glycol-co-polyethylene oxide block or random copolymers, polyethylene oxide/polypropylene oxide copolymers, sometimes referred to herein as PEO/PPO copolymers or poloxamers, including triblock PEO/PPO copolymers commercially available as PLURONICS® from BASF Corporation (Mt. Olive, N.J.), combinations thereof, and the like.

In other embodiments, suitable polyols for use as the polymeric polyol include polyester-based polyols such as polycaprolactone-based polyols including diols, polylactide-based polyols including diols, polyglycolide-based polyols including diols, combinations thereof, and the like.

In other embodiments, the polymeric core may include more than one polyalkylene oxide reacted with a dicarboxylic acid, the dicarboxylic acid including a methylene or other alkylene group, a cycloalkylene group, an aromatic group, a heteroaromatic group, or combinations thereof. Examples of such groups include, but are not limited to, methylene, ethylene, propylene, butylene, cyclohexylene, phenylene, pyridylene, combinations thereof, and the like.

In some embodiments, the polyol, including the diols described above, may be functionalized by reacting them with additional components including, but not limited to, acids such as sebacic acid, azelaic acid, suberic acid, pimelic acid, adipic acid, glutaric acid, succinic acid, malonic acid, oxalic acid, terephthalic acid, cyclohexyldicarboxylic acid, pyridine dicarboxylic acid, combinations thereof, and the like, thereby forming esters. In embodiments, PEG esters may be formed and utilized as the polymeric polyol component. In such a case, the polyol may be present in an amount of from about 66% to about 97% by weight of the ester, in embodiments from about 70% to about 90% by weight of the ester, with the acid present in an amount of from about 3% to about 34% by weight of the ester, in embodiments from about 10% to about 30% by weight of the ester.

In other embodiments, a branched polyol may be utilized to form the core, including a branched polyether diol or a branched polyester diol.

In embodiments, the polymeric polyol can have a molecular weight of from about 400 grams/mol to about 5000 grams/mol, in embodiments from about 850 grams/mol to about 2000 grams/mol.

In embodiments, the polyol can then be converted to an isocyanate prepolymer. In accordance with the present disclosure, the above polyol, such as a polyester diol or polyether diol, may be converted into an isocyanate prepolymer, in embodiments a diisocyanate prepolymer, by first converting them to nitroaryl esters or ethers. For example, a diol as described above may be reacted with a nitroaryl carboxylic acid derivative. As used herein, in embodiments, a nitroaryl carboxylic acid derivative includes an aromatic ring with at least one nitro group attached thereto, with at least one carboxylic acid group or derivative that is not directly linked to the aromatic ring. Suitable nitroaryl carboxylic acid derivatives include for example, o-nitrophenylacetic acid, m-nitrophenylacetic acid, p-nitrophenylacetic acid, o-nitrophenoxyacetic acid, m-nitrophenoxyacetic acid, p-nitrophenoxyacetic acid, 4-nitrohippuric acid, o-nitrocinnamic acid, m-nitrocinnamic acid, p-nitrocinnamic acid, combinations thereof, and the like.

In embodiments, prior to reacting the polyol with the nitroaryl carboxylic acid, the carboxylic acid group can be activated by treatment with oxalyl chloride, thionyl chloride, dicyclohexyl carbodiimide, diisopropyl carbodiimide, carbonyl diimidazole, 1-hydroxybenzotriazole, 1-(3-dimethylaminopropyl)-3-ethyl carbodiimide hydrochloride (EDCl), combinations thereof and the like. The amount of reagent added to the nitroaryl carboxylic acid derivative may be from about 1 to about 2.5 molar equivalents, in embodiments from about 1.2 to 1.6 molar equivalent.

The formation of the acid chloride may occur at temperatures of from about 0° C. to about 60° C., in embodiments from about 10° C. to about 30° C., for a period of time of from about 1 hour to about 6 hours, in embodiments from 1.5 hours to about 3 hours. The formation of the acid chloride may optionally occur with the addition of a catalyst, for example dimethyl formamide in the cases where oxalyl chloride or thionyl chloride are used as reagents.

The nitroaryl carboxylic acid derivative may be combined with the polyol to produce a nitroaryl ester by any means within the purview of those skilled in the art, including mixing, blending, combinations thereof and the like. The nitroaryl carboxylic acid derivative and the polyol may be combined at temperatures of from about 0° C. to about 80° C., in embodiments from about 25° C. to about 60° C., for a period of time from about 3 hours to 24 hours, in embodiments from about 5 hours to 16 hours. In embodiments, the reaction may occur in solution, utilizing a suitable solvent such as, for example, ethyl acetate, tetrahydrofuran (THF), dioxane, toluene, combinations thereof, and the like.

The nitroaryl ester thus produced may be recovered from solution utilizing any means within the purview of those skilled in the art, including, for example, washing and filtration, precipitation, crystallization, chromatography, combinations thereof, and the like.

The amounts of the nitroaryl carboxylic acid derivative and the polyol may be varied depending upon the desired end-use, with the nitroaryl carboxylic acid derivative present in an amount of from about 8% by weight to about 42% by weight of the nitroaryl ester, in embodiments from about 15% by weight to about 24% by weight of the nitroaryl ester, and the polyol present in an amount from about 58% by weight to about 92% by weight of the nitroaryl ester, in embodiments from 76% by weight to about 85% by weight of the nitroaryl ester.

In embodiments, the resulting nitroaryl ester or ether may then be converted to an aminoester or aminoether by a reduction reaction. Examples of suitable reducing agents for this reduction reaction include, but are not limited to, palladium with hydrogen, palladium with ammonium formate, platinum oxide with hydrogen, nickel with hydrogen, tin(II) chloride, iron with acetic acid, aluminum with ammonium chloride, borane, sodium dithionite, hydrazine, combinations thereof, and the like. The amount of reducing agent utilized to carry out the reduction reaction to form an aminoester may be from about 2 molar equivalents to about 20 molar equivalents, in embodiments about 6 molar equivalents to about 15 molar equivalents.

The reduction reaction may occur by combining the components utilizing any means within the purview of those skilled in the art, including mixing, blending, combinations thereof, and the like. The reactants utilized in the reduction reaction may optionally be heated to a temperature of from about 30° C. to about 120° C., in embodiments from about 50° C. to about 80° C. In embodiments, the reaction may occur in solution, utilizing a suitable solvent such as, for example, ethyl acetate, tetrahydrofuran, dioxane, propyl acetate, combinations thereof, and the like.

The aminoester thus produced may be recovered from solution utilizing any means within the purview of those skilled in the art including, for example, washing and filtration, precipitation, crystallization, chromatography, combinations thereof, and the like.

The resulting aminoester or aminoether may then be converted to an isocyanate ester or ether by reacting with a suitable reactant including, for example, phosgene, diphosgene, triphosgene, 4-nitrophenyl chloroformate, combinations thereof, and the like. The components utilized to form the isocyanate may be combined using any means within the purview of those skilled in the art including, for example, mixing, blending, combinations thereof, and the like. The components utilized to form the isocyanate may be optionally heated to a temperature of from about 30° C. to about 120° C., in embodiments from about 45° C. to about 80° C. The formation of the isocyanate may optionally occur in the presence of a base, such as triethylamine, pyridine, diisopropylethylamine, sodium carbonate, combinations thereof, and the like, and optionally in an aprotic solvent such as tetrahydrofuran (THF), dioxane, ethyl acetate, propyl acetate, combinations thereof, and the like.

The amount of reactants such as phosgene, diphosgene, triphosgene, 4-nitrophenylchloroformate and the like utilized to form the isocyanate may be from about 1 molar equivalent to about 3 molar equivalents, in embodiments from about 1.2 molar equivalents to about 1.75 molar equivalents, relative to the amine.

The resulting isocyanate ester or isocyanate ether, sometimes referred to, in embodiments, as a biocompatible isocyanate, may thus, in embodiments, be of the following formula combinations thereof, and n is a whole number from about 1 to about 5, in embodiments from about 2 to about 3;

$R_1$ can be $CH_2$, alkyl, $OCH_2$, $SCH_2$, $NHCH_2$, O-alkyl, S-alkyl, NH-alkyl, O-aryl, and/or NH-aryl, and $R_1$ can be the same or different at each location; and PAO is polyalkylene oxide as described above, in embodiments polyethylene glycol, having a molecular weight of from about 200 to about 4000, in embodiments from about 600 to about 2000.

In embodiments R can be methylene, ethylene, propylene, butylene, cyclohexylene, phenylene, pyridylene, combinations thereof, and the like.

The isocyanate thus produced may then be reacted with a second component to form an adhesive or sealant composition in accordance with the present disclosure. As would be readily apparent to one skilled in the art, the desired properties of the compositions of the present disclosure can be adjusted by the selection of the specific components utilized to prepare the resulting adhesive or sealant compositions.

Suitable second components that may be reacted with the biocompatible isocyanate described above (i.e., the isocyanate esters or isocyanate ethers) include those polyols described above for use in forming the polymeric core. In embodiments, the second component may include another alcohol such as, for example, glycerol, trimethylol propane, hexane-1,2,6-triol, polycaprolactone triol, polyalkylene oxides, aminoalcohols, combinations thereof, and the like. In other embodiments, the second component may also include polyamines, optionally in combination with an alcohol as described above.

Other alcohols which may be utilized include any polyol obtained by partial reaction of the polyol with, for example, polyisocyanates, polycarboxylic acid derivatives, combinations thereof, and the like, which permits the creation of longer polymeric molecules.

An adhesive composition and/or sealant composition of the present disclosure may thus possess the biocompatible isocyanate component of the present disclosure in an amount of from about 10 percent to about 100 percent by weight of the composition, in embodiments from 50 percent to 95 percent by weight of the composition, with the second component of the adhesive composition and/or sealant composition present in an amount of from about 0 percent to about 90 percent, in embodiments from 5 percent to 50 percent by weight of the composition.

In some embodiments, the weight ratio of the biocompatible isocyanate component of the present disclosure to the second component in a composition of the present disclosure may be from 5000:1 to about 1:1, in embodiments from 1000:1 to about 10:1.

The resulting composition of the present disclosure can be used in a medical/surgical capacity in place of, or in combination with, sutures, staples, clamps, combinations thereof, and the like.

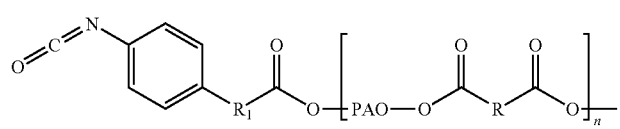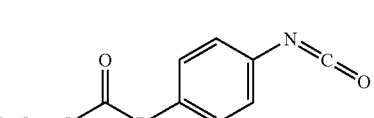

(I)

where R can be alkyl groups, cycloalkyl groups, alkenyl groups, alkynyl groups, alkylene groups, cycloalkylene groups, alkenylene groups, alkynylene groups, aromatic groups, heteroaromatic groups, heterocyclic groups, and Optional components may be added to the composition of the present disclosure to adjust its viscosity according to a specific application of use, e.g., as an adhesive or a sealant. Such optional components can include, for example, diethylene glycol dimethyl ether ("DIGLYME"), dimethylformamide ("DMF"), dimethyl succinate, dimethyl glutarate, dimethyl adipate, combinations thereof, and the like. Thickening agents which can be used to adjust the viscosity of the compositions of the present disclosure include polycyanoacrylates, polylactic acid, polyglycolic acid, lactic-glycolic acid copolymers, poly-3-hydroxybutyric acid, polyorthoesters, polyanhydrides, pectin, combinations thereof, and the like.

Where utilized, such additives can be included so that they are present in an amount of from about 1 to about 30 percent by weight of the composition, in embodiments from about 2 to about 15 percent by weight of the composition.

Optionally, stabilizers can also be added to increase the storage stability of the compositions of the present disclosure. Suitable stabilizers can include those which prevent premature polymerization such as quinones, hydroquinone, hindered phenols, hydroquinone monomethyl ether, catechol, pyrogallol, benzoquinone, 2-hydroxybenzoquinone, p-methoxy phenol, t-butyl catechol, butylated hydroxy anisole, butylated hydroxy toluene, t-butyl hydroquinone, combinations thereof, and the like. Suitable stabilizers can also include anhydrides, silyl esters, sultones (e.g., α-chloro-α-hydroxy-o-toluenesulfonic acid-γ-sultone), sulfur dioxide, sulfuric acid, sulfonic acid, sulfurous acid, lactone, boron trifluoride, organic acids, alkyl sulfate, alkyl sulfite, 3-sulfolene, alkylsulfone, alkyl sulfoxide, mercaptan, alkyl sulfide, combinations thereof, and the like. In some embodiments, an anhydride such as maleic anhydride, sebacic acid anhydride, and/or azelaic acid anhydride, can be used as a stabilizer. In other embodiments antioxidants such as Vitamin E, Vitamin K1, cinnamic acid, and/or flavanone can be used as stabilizers.

Where utilized, such stabilizers can be included so that they are present in an amount from about 0.01 to about 10 percent by weight of the composition, in embodiments from about 0.1 to about 2 percent by weight of the composition.

In some embodiments, solid supported catalysts may be used during synthesis to improve stability of the resulting composition of the present disclosure. The presence of such catalysts may increase reactivity during use. Suitable catalysts are within the purview of those skilled in the art and can include stannous octoate, triethylamine, diethylaminoethanol, dimethylaminopyridine (DMAP), combinations thereof, and the like. The amount of catalyst employed can be from about 0.5 grams to about 50 grams per kilogram of the other components of the composition.

The compositions of the present disclosure can be used for a number of different human and animal medical applications including, but not limited to, wound closure (including surgical incisions and other wounds), adhesives for medical devices (including implants), void fillers, and embolic agents. Adhesive compositions and/or sealant compositions may be used to bind tissue together either as a replacement of, or as a supplement to, sutures, staples, clamps, tapes, bandages, and the like. Use of the disclosed compositions can eliminate or substantially reduce the number of sutures normally required during current practices, and eliminate the subsequent need for removal of staples and certain types of sutures. The compositions of the present disclosure thus can be particularly useful for use with delicate tissues where sutures, clamps or other conventional tissue closure mechanisms may cause further tissue damage.

Application of the compositions of the present disclosure, with or without other additives, can be done by any conventional means. These include dipping, brushing, or other direct manipulation of the composition on the tissue surface, by syringe, such as with a mixer nozzle, or spraying of the composition onto the surface. In open surgery, application by hand, forceps, or the like is contemplated. In endoscopic surgery, the composition can be delivered through the cannula of a trocar, and spread at the site by any device within the purview of those skilled in the art.

In embodiments, the biocompatible isocyanate component of the present disclosure, optionally in combination with the second component, may be dissolved in a solvent to form a solution for application. Suitable solvents include those that are water miscible and biologically acceptable for medical/surgical use. In some embodiments, the solvents can include DIGLYME (diethylene glycol dimethyl ether), N,N-dimethylformamide ("DMF"), dimethyl sulfoxide, combinations thereof, and the like.

In embodiments, the biocompatible isocyanate component may be in a first solution, with the at least one second component dissolved in an aqueous media which optionally contains at least one biodegradable thickener. Suitable biologically acceptable thickeners include disaccharides, polysaccharides, alginates, hyaluronic acid, pectins, dextrans, cellulosics such as carboxymethyl cellulose, methyl cellulose, combinations thereof, and the like.

The biocompatible isocyanate component may be present in the first solution in an amount from about 10% to about 100% by weight of the first solution, in embodiments from about 50% to about 90% by weight of the first solution. The amount of second component in the aqueous media, sometimes referred to herein as a second solution, may be from about 0.01% to about 10% by weight of the second solution, in embodiments from about 0.05% to about 5% by weight of the second solution. Where present, a biodegradable thickener may be present in an amount from about 0% to about 10% by weight of the second solution.

The biocompatible isocyanate component solution and the second component solution may then be combined upon application to form a sealant or adhesive composition of the present disclosure. For example, the composition of the present disclosure can be dispensed from a conventional adhesive dispenser, which may provide mixing of the biocompatible isocyanate component and second component prior to dispensing the adhesive or sealant. Such dispensers are disclosed, for example, in U.S. Pat. Nos. 4,978,336, 4,361,055, 4,979,942, 4,359,049, 4,874,368, 5,368,563, and 6,527,749, the disclosures of each of which are incorporated by reference herein.

In some embodiments, a dual-compartment applicator may be utilized and mixing of the biocompatible isocyanate component solution and second component solution may occur to form an adhesive upon dispensing by an aerosol or by means of a mixing head attached to the applicator or syringe. Other additives can be introduced into the biocompatible isocyanate component solution, the second component solution, or both.

For example, the adhesive composition may be sprayed onto mammalian tissue, which lowers the risk of additional mechanical stress on the tissue. The spray application can be by any means within the purview of those skilled in the art such that the composition can be applied as a fine mist or aerosol. For example, the composition can be placed in a spray bottle and delivered with a hand pump. Alternatively, the composition can be placed in a container with a non-chlorofluorohydrocarbon propellant (e.g., air, nitrogen, carbon dioxide, and/or hydrocarbons) and delivered using a pressurized spray can. In either case, the composition is passed through a fine orifice to form a mist and delivered to the surgical location.

In other embodiments, especially where the composition of the present disclosure is to be utilized as a void filler or to fill a defect in an animal's body, it may be advantageous to more precisely control the conditions and extent of cross-linking; in such a case, it may be desirable to partially cross-link the composition prior to its use to fill a void in animal tissue. The composition of the present disclosure may then be applied to the void or defect and allowed to set, thereby filling the void or defect.

To effectuate the joining of two tissue edges, the two edges may be approximated, and the biocompatible isocyanate component may be applied in combination with the second component. In other embodiments, the biocompatible isocyanate component may be applied to one tissue edge, the second component may be applied to a second tissue edge, and the two edges then brought into contact with each other. The components crosslink rapidly, generally taking less than one minute. The composition of the present disclosure can thus be used as an adhesive to close a wound, including a surgical incision. In such a case, the composition of the present disclosure can be applied to the wound and allowed to set, thereby closing the wound.

In another embodiment, the present disclosure is directed to a method for using the adhesive composition of the present disclosure to adhere a medical device to tissue, rather than secure two edges of tissue. In some aspects, the medical device includes an implant. Other medical devices include, but are not limited to, pacemakers, stents, shunts and the like. In some embodiments, depending on the composition of the medical device, a coating may be required on the medical device. In some aspects such a coating can include the biocompatible isocyanate component of the present disclosure in combination with the second component. Generally, for adhering a device to the surface of animal tissue, the composition of the present disclosure can be applied to the device, the tissue surface, or both. In other embodiments, the biocompatible isocyanate component of the present disclosure can be applied to either the device or the tissue surface, with the second component applied to the other (i.e., where the biocompatible isocyanate component has not been applied). The device and tissue surface are then brought into contact with each other and the composition is allowed to set, thereby adhering the device and tissue surface to each other.

The composition of the present disclosure can also be used to prevent post surgical adhesions. In such an application, the composition may be applied and cured as a layer on surfaces of internal tissues in order to prevent the formation of adhesions at a surgical site during the healing process. In addition to the formation of adhesion barriers, in embodiments the adhesive may be utilized to form implants such as gaskets, buttresses or pledgets for implantation.

In another embodiment, the composition can be used to attach skin grafts and position tissue flaps during reconstructive surgery. In still another embodiment, the composition can be used to close tissue flaps in periodontal surgery.

Applications for the compositions of the present disclosure also include sealing tissues to prevent or control blood or other fluid leaks at suture or staple lines. In embodiments, the composition can be used to seal or adhere delicate tissue together in place of conventional tools that may cause mechanical stress. The composition can also be used to seal air and/or fluid leaks in tissue. Additionally, the composition can be applied to tissue as a barrier to prevent adhesions, provide a protective layer for delicate damaged tissue and/or provide a drug delivery layer to a surgical site.

When used as a sealant, the composition of the present disclosure can be used in surgery to prevent or inhibit bleeding or fluid leakage both during and after a surgical procedure. It can also be applied to prevent air leaks associated with pulmonary surgery. The sealant may be applied directly to the desired area in at least an amount necessary to seal off any defect in the tissue and seal off any fluid or air movement.

A variety of optional ingredients, including medicinal agents, may also be added to the compositions of the present disclosure. These agents may be added to adhesive compositions of the present disclosure, sealant compositions of the present disclosure, or both. Additional medicinal agents include antimicrobial agents, colorants, preservatives, or medicinal agents such as, for example, protein and peptide preparations, antipyretic, antiphlogistic and analgesic agents, anti-inflammatory agents, vasodilators, antihypertensive and antiarrhythmic agents, hypotensive agents, antitussive agents, antineoplastics, local anesthetics, hormone preparations, antiasthmatic and antiallergic agents, antihistaminics, anticoagulants, antispasmodics, cerebral circulation and metabolism improvers, antidepressant and antianxiety agents, vitamin D preparations, hypoglycemic agents, antiulcer agents, hypnotics, antibiotics, antifungal agents, sedative agents, bronchodilator agents, antiviral agents, dysuric agents, combinations thereof, and the like. A phospholipid surfactant that provides antibacterial stabilizing properties and helps disperse other materials in the compositions may also be added to the compositions of the present disclosure.

Imaging agents such as iodine, barium sulfate, or fluorine, can also be combined with the compositions of the present disclosure to allow visualization of the surgical area through the use of imaging equipment, including X-ray, MRI, and/or CAT scan.

Additionally, an enzyme may be added to the compositions of the present disclosure to increase their rate of degradation. Suitable enzymes include, for example, peptide hydrolases such as elastase, cathepsin G, cathepsin E, cathepsin B, cathepsin H, cathepsin L, trypsin, pepsin, chymotrypsin, γ-glutamyltransferase (γ-GTP), and the like; sugar chain hydrolases such as phosphorylase, neuraminidase, dextranase, amylase, lysozyme, oligosaccharase, and the like; oligonucleotide hydrolases such as alkaline phosphatase, endoribonuclease, endodeoxyribonuclease, and the like. In some embodiments, where an enzyme is added, the enzyme may be included in a liposome or microsphere to control the rate of its release, thereby controlling the rate of degradation of the composition of the present disclosure. Methods for incorporating enzymes into liposomes and/or microspheres are within the purview of those skilled in the art.

The present compositions have a number of advantageous properties. The resulting compositions of the present disclosure are safe and biocompatible, possess enhanced adherence to tissue, are biodegradable, have hemostatic potential, have low cost, and are easy to prepare and use. The compositions also have a rapid curing time. Application of the compositions, with or without other additives, can be done by any conventional means. By varying the selection of the components, the strength and elasticity of the adhesive and/or sealant composition can be controlled, as can the gelation time.

The compositions rapidly form a compliant gel matrix, which insures stationary positioning of tissue edges or implanted medical devices in the desired location where the composition is utilized as an adhesive, and a tightly adherent yet flexible seal where the composition is used as a sealant. In either case, the rapidity of gelation lowers the overall required surgical/application time. Where delicate or spongy tissues are involved and/or air or fluid leaks must be sealed, spray application of a composition may be utilized to avoid stress to the tissue and insure a uniform coating over the area.

The compositions of the present disclosure retain the positional integrity of the tissue to which they are applied and/or location of a medical device. The compositions form strong cohesive bonds. They exhibit excellent mechanical performance and strength, while retaining the necessary pliability to adhere living tissue. This strength and pliability allows a degree of movement of tissue without shifting the surgical tissue edge. Additionally, the compositions are biodegradable, allowing the degradation components to pass safely through the subject's body.

The following Examples are being submitted to illustrate embodiments of the present disclosure. The Examples are intended to be illustrative only and are not intended to limit the scope of the present disclosure. Also, parts and percentages are by weight unless otherwise indicated. As used herein, "room temperature" refers to a temperature of from about 20° C. to about 25° C.

EXAMPLE 1

A solution of p-nitrophenylacetic acid (about 12.02 grams) in THF (about 130 ml) at room temperature was treated with oxalyl chloride (about 12.25 grams) and two drops of N,N-dimethylformamide. The resulting mixture was stirred at room temperature for about 1.5 hours and then evaporated to dryness using a rotary evaporator. The resulting acid chloride was mixed with about 50 grams of polyethylene glycol adipate ($M_w$ about 1658). The mixture was heated at about 70° C. for about 16 hours. After cooling to room temperature, it was diluted with THF (about 100 ml), treated with activated carbon (about 2 grams) and CELITE® (about 10 grams). After stirring for about 15 minutes, the mixture was filtered over a pad of CELITE® and washed with THF (about 50 ml). The filtrate was evaporated under reduced pressure. The residue was further dried under vacuum and gave the bis p-nitrophenylacetic acid ester.

The chemical structure was confirmed by $^1$H-NMR and $^{13}$C NMR. A summary of this reaction is provided below as formula II.

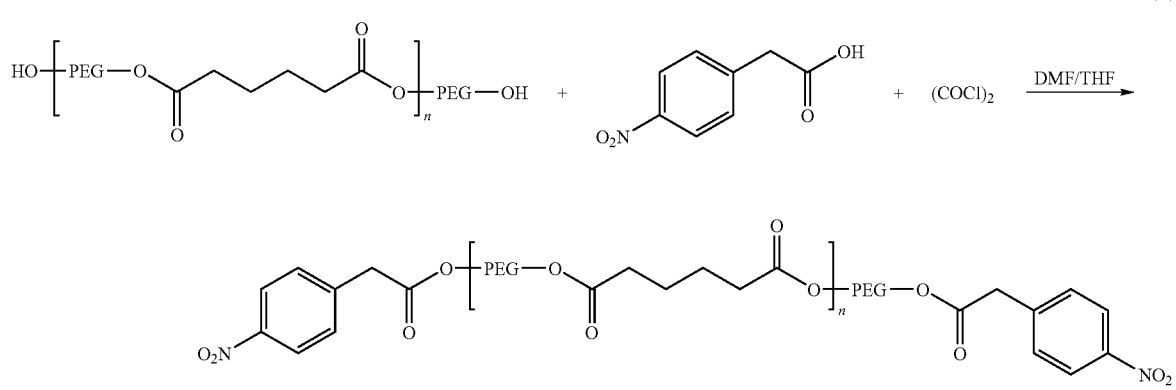

EXAMPLE 2

A solution of the p-nitrophenylacetate (about 60 grams) produced in Example 1 above in THF (about 300 ml) was successively treated with about 10% palladium on carbon (about 1.61 grams) and ammonium formate (about 19.1 grams). The resulting mixture was heated at about 60° C. for about 2 hours. After cooling to room temperature, the reaction mixture was filtered over CELITE® and the filtrate was evaporated. The residue was partitioned between brine (about 100 ml) and ethyl acetate (about 350 ml). The organic phase was dried over magnesium sulfate, filtered and evaporated to give the corresponding p-aminophenyl acetic ester. Its chemical structure was confirmed by $^1$H-NMR and $^{13}$C NMR. A summary of this reaction is provided below as formula III.

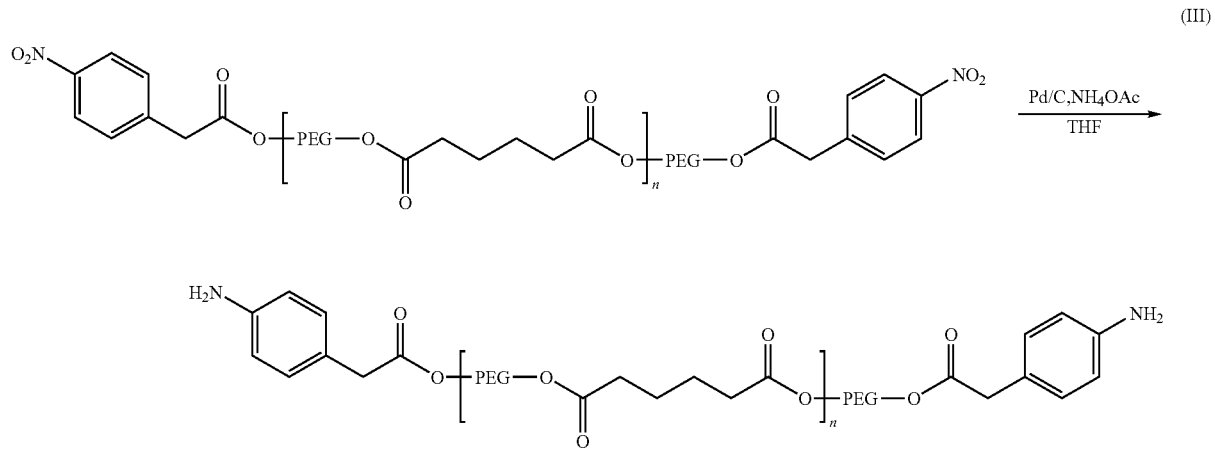

EXAMPLE 3

A solution of the p-aminophenylacetyl ester produced in Example 2 (about 57.3 grams) in THF (about 100 ml) was slowly added using an addition funnel to a solution of triphosgene (about 6.63 grams) in THF (about 200 ml) at room temperature. The reaction mixture was heated at about 65° C. overnight. The reaction mixture was evaporated and the residue was analyzed by NMR and IR and identified as the isocyanate prepolymer of the invention. A summary of this reaction is provided below as formula IV.

After sterilization by γ-irradiation, the resulting adhesive/sealant had an isocyanate content of about 2.47%, a viscosity of about 34905 centipoise and a lap shear of about 1238 grams.

EXAMPLE 5

A solution of about 11.8 grams of p-nitrophenoxyacetic acid in about 80 ml of THF was treated with about 9.5 grams of oxalyl chloride and a few drops of dimethylformamide. The resulting solution was stirred at room temperature for about 1.5 hours and evaporated to dryness to give the corresponding acid chloride. The acid chloride was combined with about 40 grams of PEG-adipate ($M_n$ about 1608) and the

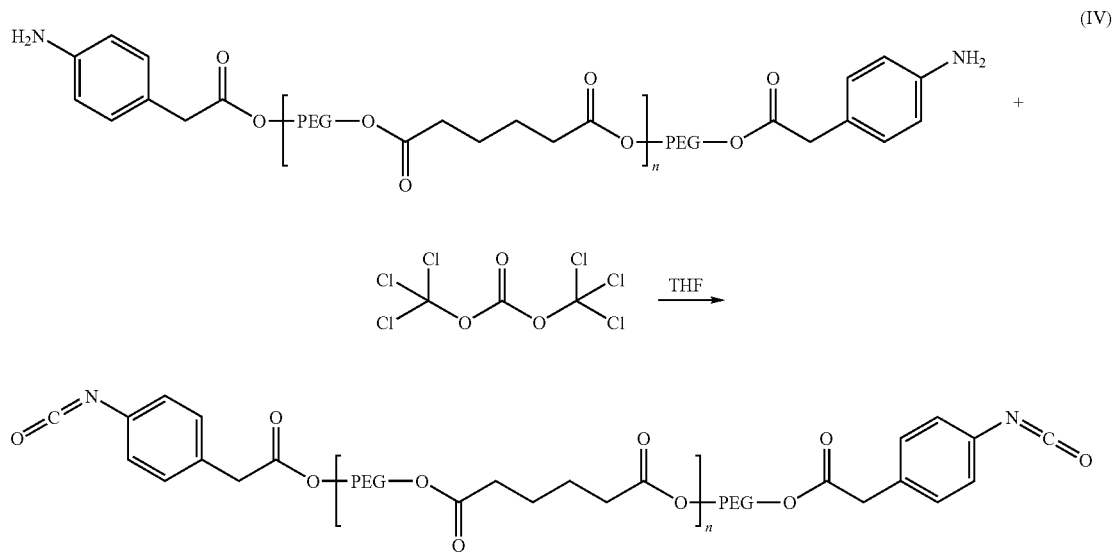

EXAMPLE 4

The diisocyanate prepolymer (about 45.5 grams, about 4.41% NCO content) prepared in Example 3 was placed in a 3-neck flask round bottom flask and treated with trimethylolpropane (about 0.71 grams). The resulting mixture was heated at about 65° C. for about 16 hours and packaged into syringes. A summary of this reaction is provided below as formula V.

resulting mixture was heated at about 60° C. for about 16 hours. The reaction mixture was diluted in about 150 ml of THF and treated with about 2 grams of activated carbon and about 10 grams of CELITE®. The mixture was stirred for about 15 minutes, then filtered over CELITE®, washed with about 50 ml of THF and evaporated. The residue, which was about 40.6 grams of the p-nitrophenoxyacetate ester, was dried under vacuum and its structure was confirmed by NMR. A summary of this reaction is provided below as formula VI.

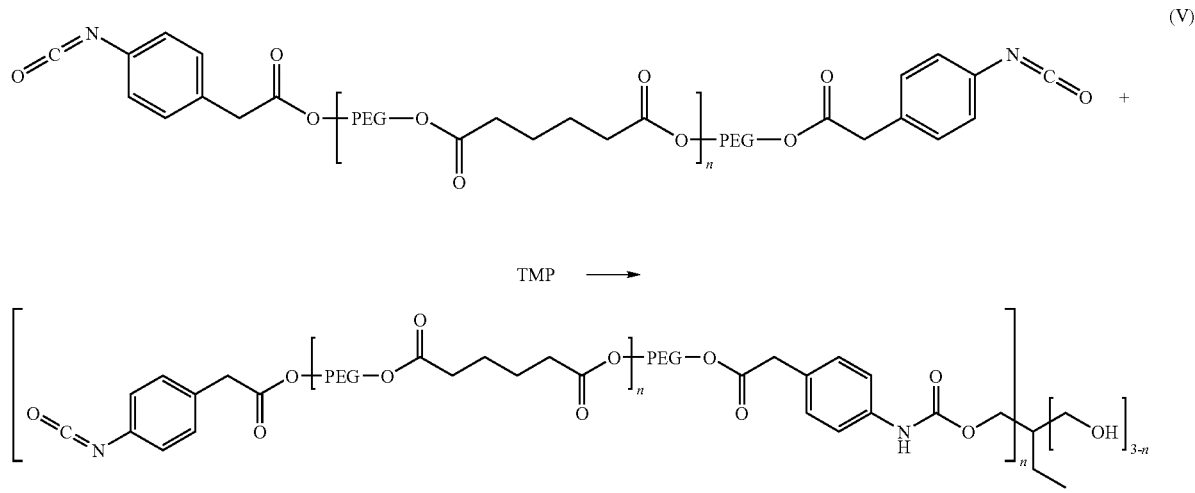

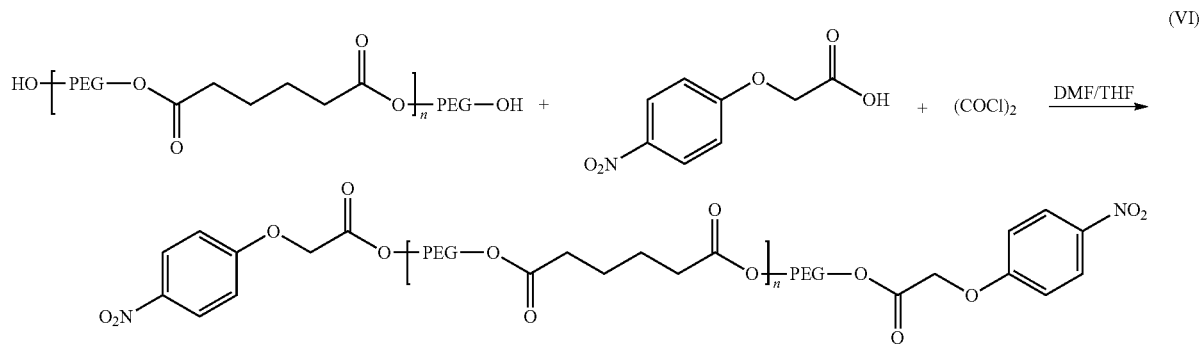

(VI)

EXAMPLE 6

A solution of the p-nitrophenoxyacetate (about 40.55 grams) produced in Example 5 above in THF (about 150 ml) was successively treated with about 10% palladium on carbon (about 1.11 grams) and ammonium formate (about 13.2 grams). The resulting mixture was heated at about 60° C. for about 16 hours. After cooling to room temperature, the reaction mixture was filtered over about 2 cm of packed alumina in a 350 ml fitted funnel and the filtrate was evaporated. The organic phase was dried over magnesium sulfate, filtered, and evaporated to give the corresponding p-aminophenoxyacetate ester.

Its chemical structure was confirmed by $^1$H-NMR. A summary of this reaction is provided below as formula VII.

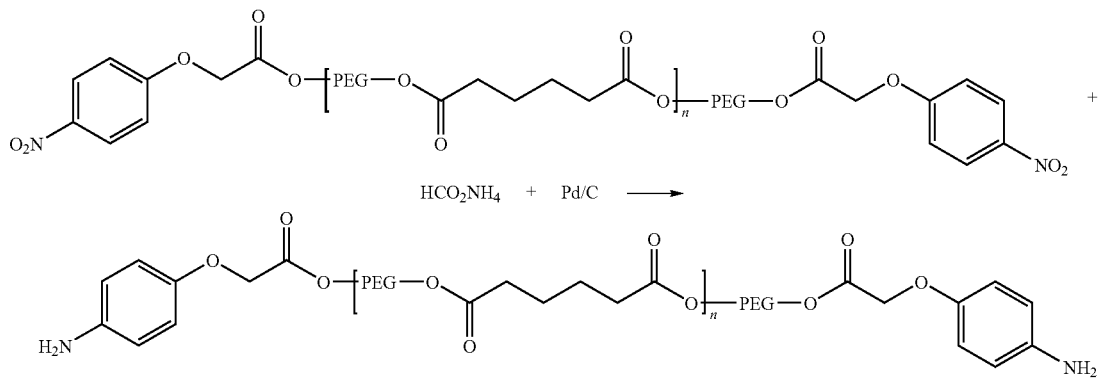

(VII)

EXAMPLE 7

A solution of the p-aminophenoxyacetate ester produced in Example 6 (about 25.85 grams) in THF (about 35 ml) was slowly added using an addition funnel to a solution of triphosgene (about 2.32 grams) in THF (about 25 ml) at room temperature. The reaction mixture was heated at about 65° C. overnight. The reaction mixture was evaporated and the residue was analyzed by NMR and IR and identified as the isocyanate prepolymer of the invention. A summary of this reaction is provided below as formula VIII.

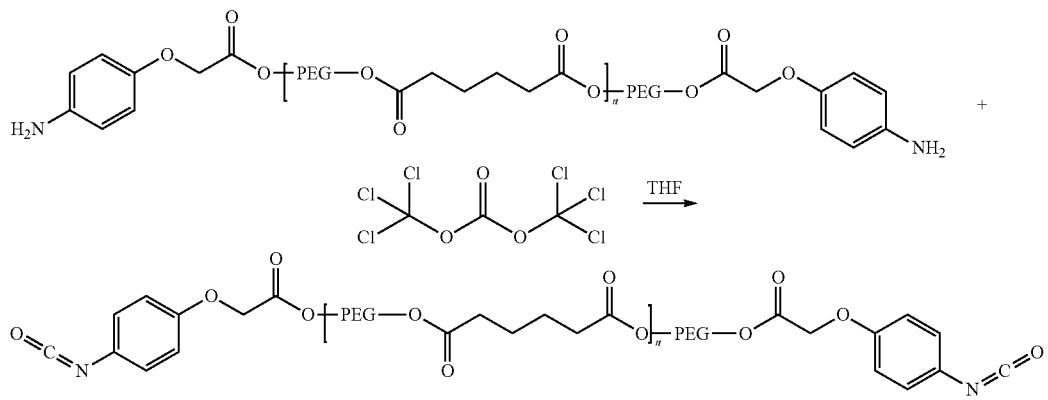

(VIII)

EXAMPLE 8

The diisocyanate prepolymer (about 18.74 grams, about 3.66% NCO content) prepared in Example 7 was placed in a 3-neck flask round bottom flask and treated with trimethylolpropane (about 0.24 grams). The resulting mixture was heated at about 65° C. for about 16 hours and afforded the branched material. A summary of this reaction is provided below as formula IX.

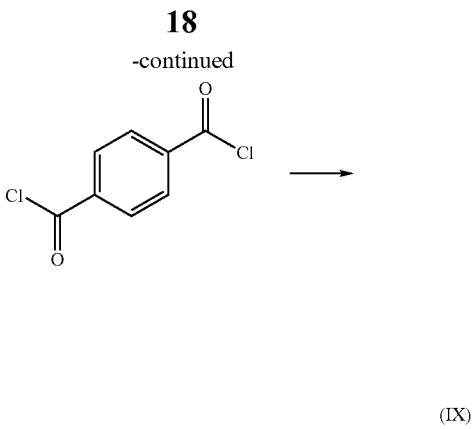

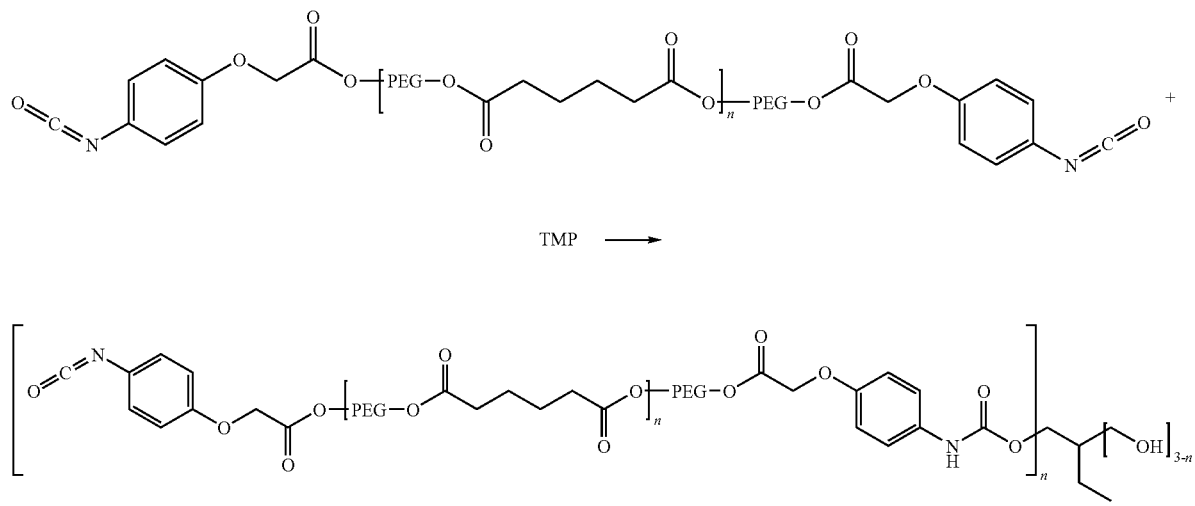

EXAMPLE 9

About 155.32 grams of polyethylene glycol was dried by heating at about 105° C. and bubbling nitrogen through the material for about 4 hours. After cooling to room temperature, it was treated with about 28.9 grams of terephthaloyl chloride. The mixture was heated at about 65° C. and kept at that temperature for about 20 hours. The reaction mixture was diluted with about 450 ml of THF, transferred into a separatory funnel and washed with about 200 ml of brine. The two phases were separated and the aqueous phase was extracted with about 100 ml of THF. The combined organic phase was dried over magnesium sulfate and alumina and filtered. The filtrate was evaporated under reduced pressure and the residue was further dried under high vacuum to provide polyethylene glycol terephthalate. A summary of this reaction is provided below as formula X.

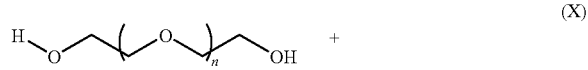

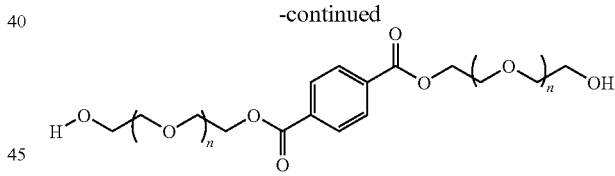

EXAMPLE 10

A solution of about 6.72 grams of p-nitrophenylacetic acid in about 50 ml of THF was treated with about 6.43 grams of oxalyl chloride and a few drops of dimethylformamide. The resulting solution was stirred at room temperature for about 1.5 hours and evaporated to dryness to give the corresponding acid chloride. The acid chloride was combined with about 30 grams of PEG-terephthalate ($M_n$ about 1778) and the resulting mixture was heated at about 60° C. for about 16 hours. The reaction mixture was diluted with about 150 ml of THF and treated with about 10 grams of magnesium sulfate, about 2 grams of activated carbon and about 10 grams of CELITE®. The mixture was stirred for about 15 minutes, then filtered over CELITE®, washed with about 50 ml of THF and evaporated. The residue, which was the p-nitrophenylacetate ester, was dried under vacuum and its structure was confirmed by NMR. A summary of this reaction is provided below as formula XI.

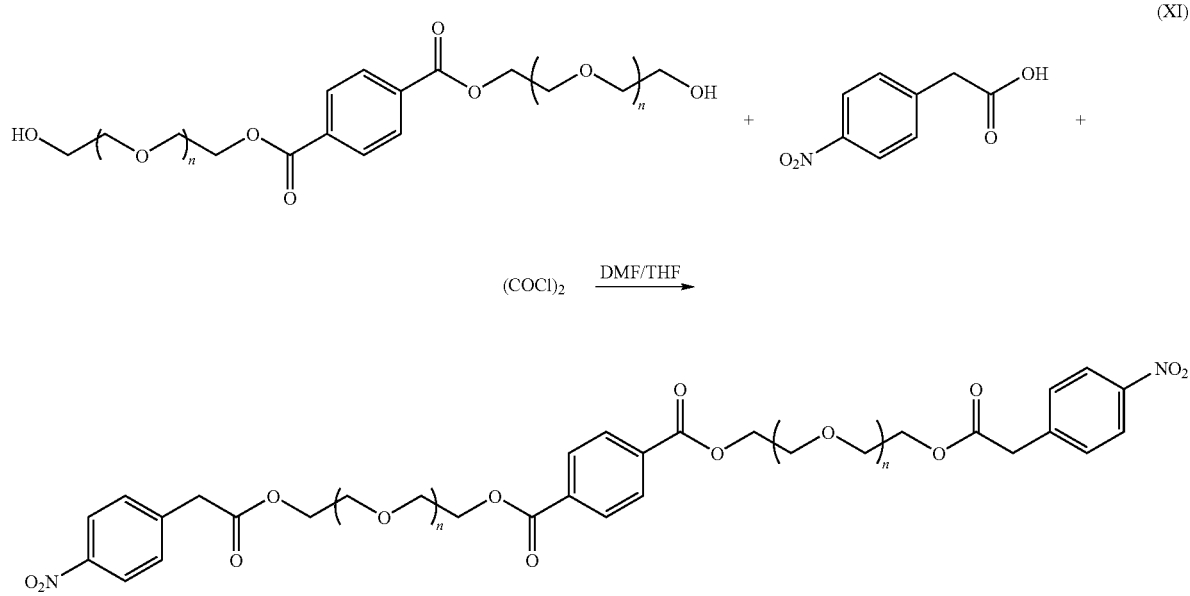

EXAMPLE 11

A solution of the p-nitrophenylacetate (about 36.7 grams) produced in Example 10 above in THF (about 150 ml) was successively treated with about 10% Palladium on carbon (about 0.93 grams) and ammonium formate (about 11 gram). The resulting mixture was heated overnight at about 60° C. After cooling to room temperature, the reaction mixture was treated with magnesium sulfate (about 10 grams), CELITE® (about 5 grams) and activated carbon (about 1 gram), and stirred for about 15 minutes. It was then filtered over CELITE® and washed with about 300 ml of THF. The filtrate was evaporated and dried under high vacuum providing the p-amino-phenylacetate. A summary of this reaction is provided below as formula XII.

EXAMPLE 12

About 3.92 grams of triphosgene was placed in a 250 ml 3-neck round bottom flask equipped with a mechanical stirrer, a condenser and an addition funnel under static nitrogen. About 50 ml of THF was added. After complete dissolution of triphosgene, a solution of about 36 grams of the phenylacetylamino ester from Example 11 in about 100 ml of THF was added dropwise. The resulting mixture was heated at about 65° C. for about 16 hours. The THF evaporated overnight under the flow of nitrogen, leaving the desired diisocyanate prepolymer. Its structure was confirmed by $^1$H NMR and IR analyses. A summary of this reaction is provided below as formula XIII.

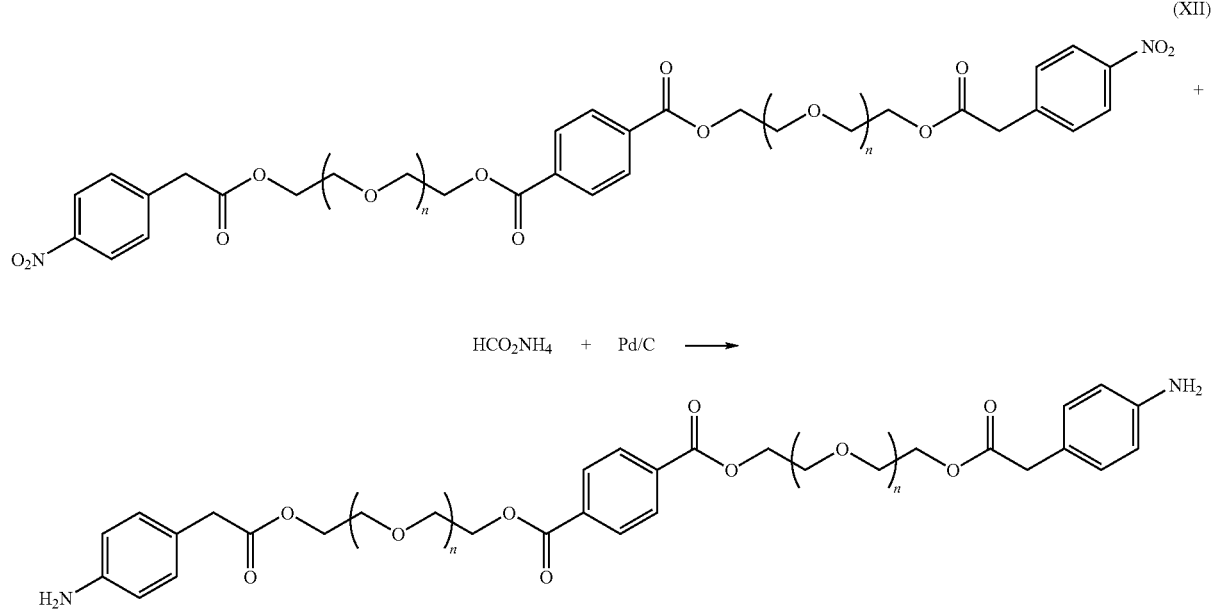

(XIII)

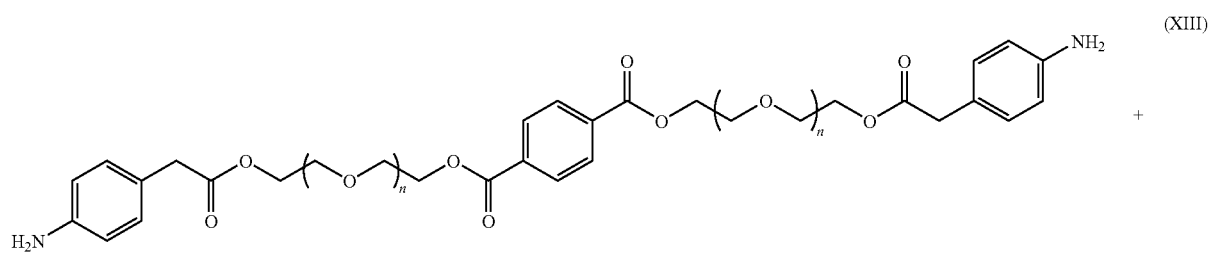

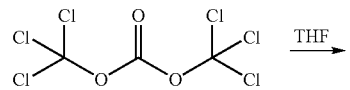

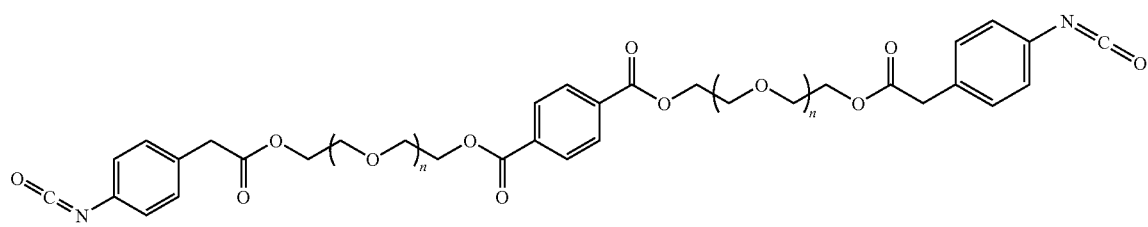

EXAMPLE 13

About 14.98 grams of the diisocyanate prepolymer produced in Example 12 was placed in a 3-neck round bottom flask and treated with about 0.21 grams of trimethylol propane. The mixture was heated to about 65° C. and kept at that temperature for about 20 hours to generate the adhesive/sealant of the present disclosure. The resulting material had an NCO content of about 1.94%, a viscosity of about 365.5 kilocentipoise and a lap shear of about 266 grams. A summary of this reaction is provided below as formula XIV.

EXAMPLE 14

About 11.98 grams of m-nitrophenoxyacetic acid was dissolved in about 150 ml of THF and the solution was treated with about 11.22 grams of oxalyl chloride, followed by a couple of drops of dimethyl formamide. The resulting mixture was stirred at room temperature for about 1.5 hours, then evaporated to dryness to obtain the corresponding acid chloride. The acid chloride was then combined with about 46 grams of PEG-adipate. The mixture was heated at about 60° C. for about 20 hours. After cooling to room temperature, the reaction mixture was diluted with about 300 ml of THF, (XIV)

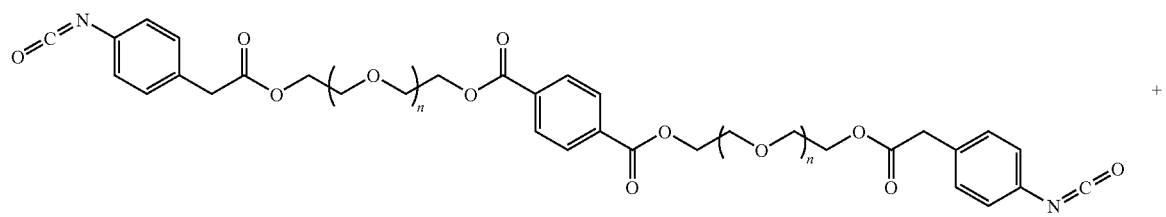

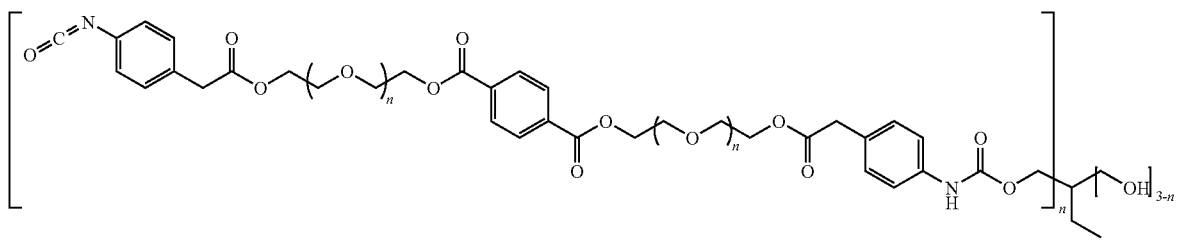

treated with alumina, CELITE® and magnesium sulfate, and stirred for about 15 minutes. It was then filtered over CELITE® and evaporated. The residue was further dried under high vacuum to provide about 41.7 grams of the corresponding m-nitrophenoxyacetate ester of PEG-adipate. A summary of this reaction is provided below as formula XV.

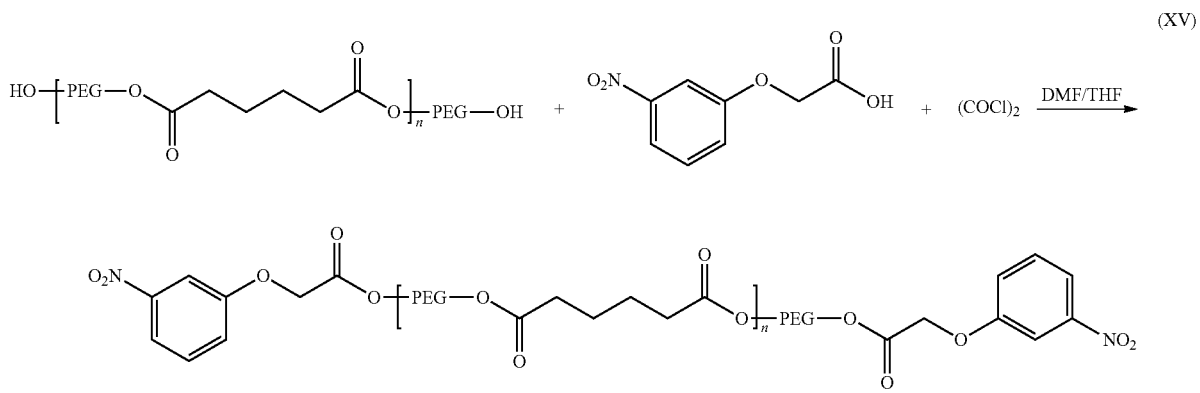

(XV)

EXAMPLE 15

About 41.7 grams of m-nitrophenoxyacetate produced in Example 14 was dissolved in about 300 ml of THF and treated with about 1.2 grams of palladium on carbon and about 14.27 grams of ammonium formate. The mixture was heated at about 60° C. and kept at that temperature for about 3 hours. The mixture was treated with about 10 grams of magnesium sulfate, about 5 grams of CELITE®, and about 1 gram of activated carbon and stirred for about 15 minutes. It was then filtered over CELITE® and washed with about 250 ml of THF. The filtrate was evaporated under reduced pressure and further dried under high vacuum to provide the desired m-aminophenoxyacetate. A summary of this reaction is provided below as formula XVI.

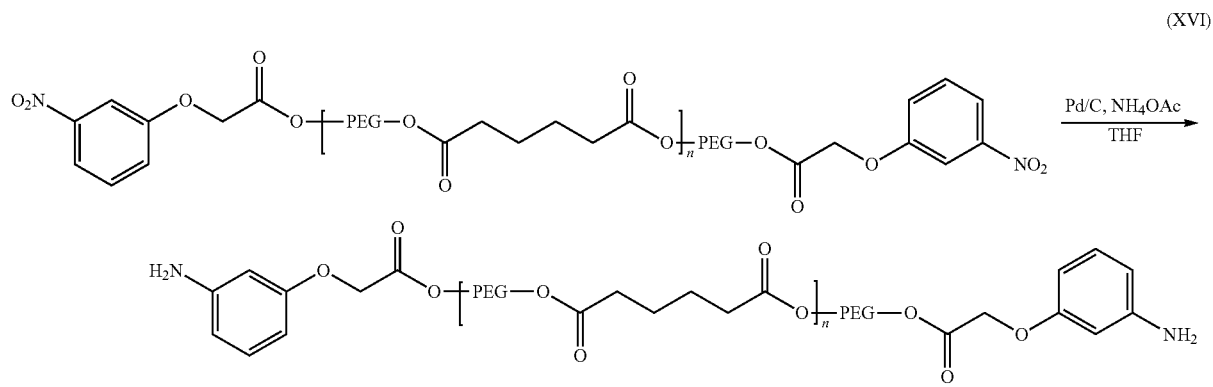

(XVI)

EXAMPLE 16

About 4.97 grams of triphosgene was added to about 100 ml of THF in a 500 ml, 3-neck round bottom flask under static nitrogen, equipped with a mechanical stirrer, a condenser and an addition funnel. A solution of about 39.8 grams of the m-amino-phenoxyacetate ester produced in Example 15 in about 100 ml of THF was added using the addition funnel. The resulting mixture was heated at about 65° C. under a flow of nitrogen for about 20 hours providing the diisocyanate prepolymer. Its structure was confirmed by NMR and IR. A summary of this reaction is provided below as formula XVII.

(XVII)

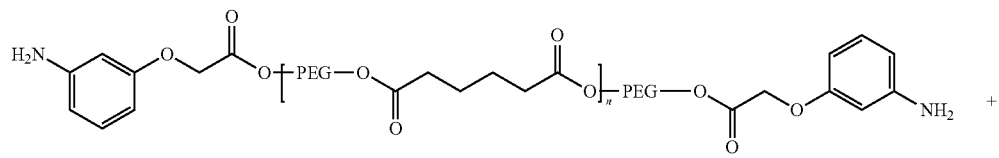

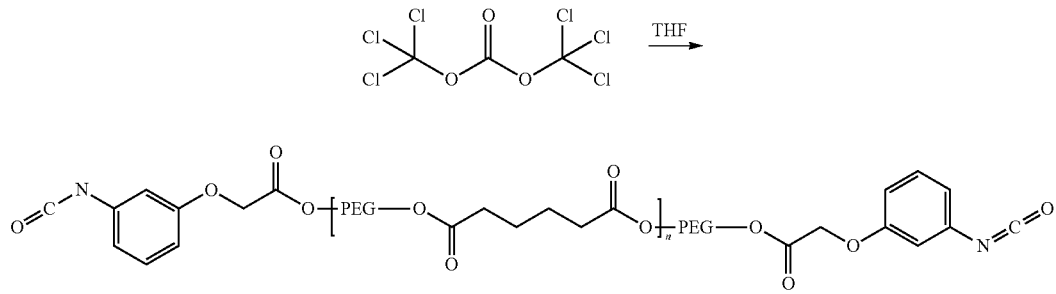

EXAMPLE 17

About 16.54 grams of the diisocyanate prepolymer produced in Example 16 was placed in a dry 3-neck round bottom flask and treated with about 0.21 grams of trimethylol propane. The mixture was heated to about 65° C. and kept at that temperature for about 20 hours, providing the adhesive/sealant of the present disclosure. The resulting material had an NCO content of about 2.92%, a viscosity of about 15 kilocentipoise and a lap shear of about 352 grams.

A second reaction was performed under the same conditions by reacting about 18.92 grams of the diisocyanate ester of Example 16 with about 0.35 grams of trimethylol propane. The resulting material had an NCO content of about 2.54%, a viscosity of about 35.4 kilocentipoise and a lap shear of about 1020 grams. A summary of this reaction is provided below as formula XVIII.

EXAMPLE 18

A solution of about 8.21 grams of p-nitrophenoxyacetic acid in about 60 ml of THF was successively treated with about 7.85 grams of oxalyl chloride followed by a couple of drops of dimethyl formamide. The resulting solution was stirred at room temperature for about 1.5 hours and evaporated under reduced pressure to provide the corresponding acid chloride. The acid chloride was then combined with about 38.9 grams of polyethylene glycol-cyclohexyldicarboxylate (PEG-cyclohexyldicarboxylate). The mixture was then heated at about 60° C. for about 20 hours. The reaction was diluted with about 150 ml of THF and treated with about 2 grams of activated carbon, about 10 grams of magnesium sulfate, and about 5 grams of CELITE®, and stirred for about 15 minutes. The mixture was then filtered over CELITE® and washed with about 50 ml of THF. The filtrate was evaporated under reduced pressure and further dried under high vacuum to give the p-nitrophenylacetyl ester. A summary of this reaction is provided below as formula XIX.

(XVIII)

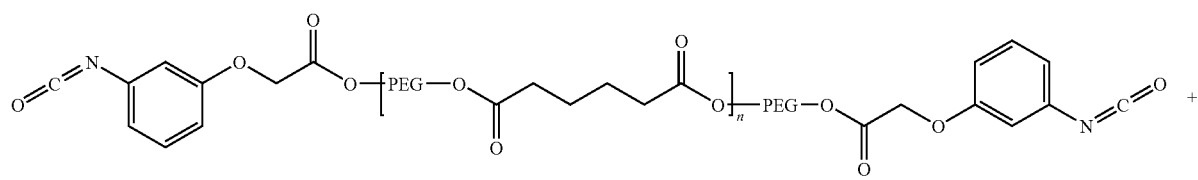

TMP ⟶

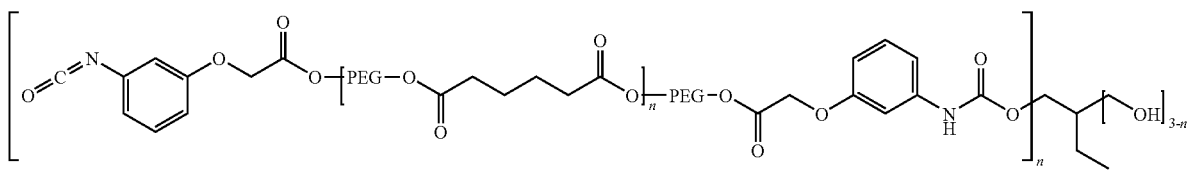

(XIX)

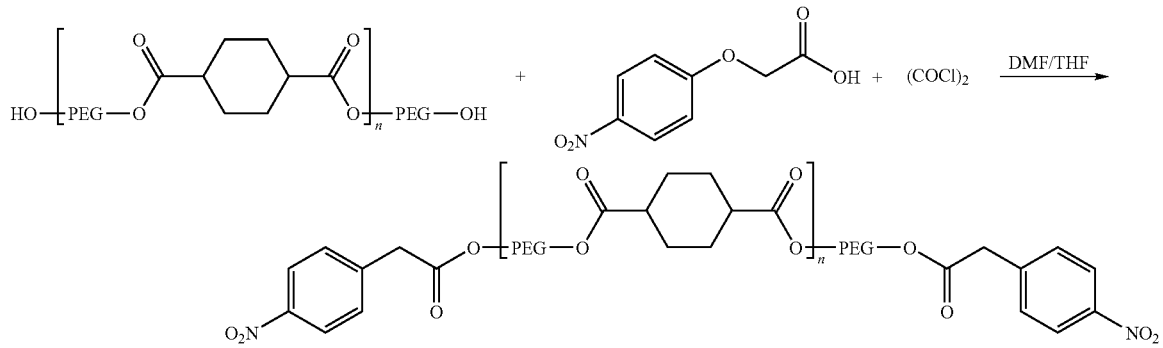

EXAMPLE 19

A solution of about 39.2 grams of the p-nitrophenylacetyl ester produced in Example 18 in about 200 ml of THF was successively treated with about 0.94 grams of palladium on carbon and about 11.17 grams of ammonium formate. The mixture was heated at about 60° C. and kept at that temperature from about 12 to about 20 hours. The mixture was treated with about 2 grams of activated carbon, about 10 grams of magnesium sulfate and about 5 grams of CELITE®, and stirred for about 15 minutes. It was then filtered over CELITE® and washed with about 250 ml of THF. The filtrate was evaporated under reduced pressure, then dried under high vacuum to provide the corresponding p-aminophenylacetate. A summary of this reaction is provided below as formula XX.

(XX)

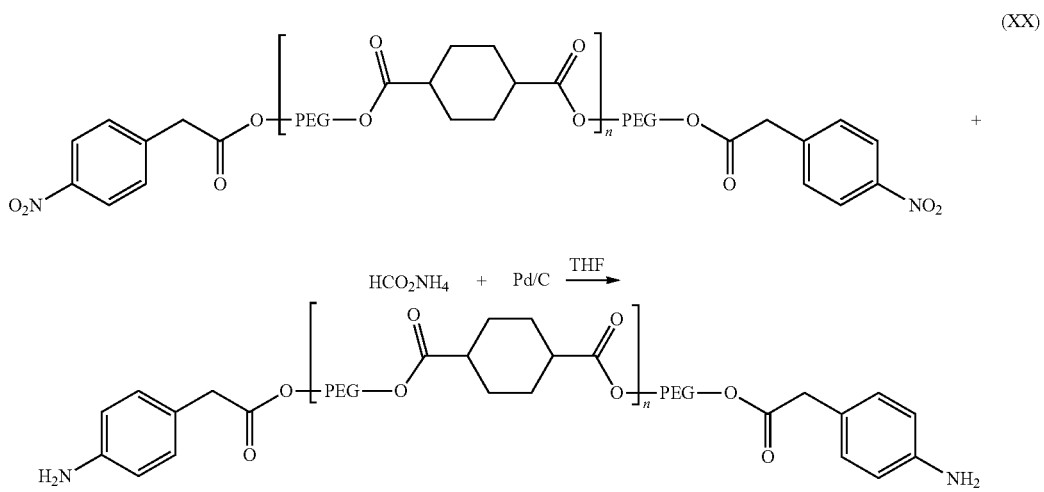

EXAMPLE 20

A solution of about 3.56 grams of triphosgene in about 250 ml of THF was placed in a 3-neck round bottom flask under static nitrogen equipped with a mechanical stirrer, a condenser and an addition funnel. To this, a solution of about 34.45 grams of the p-aminophenylacetate produced in Example 19 in about 120 ml of THF was added using the addition funnel. The mixture was heated at about 65° C. and kept at that temperature for a time of from about 16 to about 20 hours. The THF was evaporated, providing the corresponding diisocyanate prepolymer. A summary of this reaction is provided below as formula XXI.

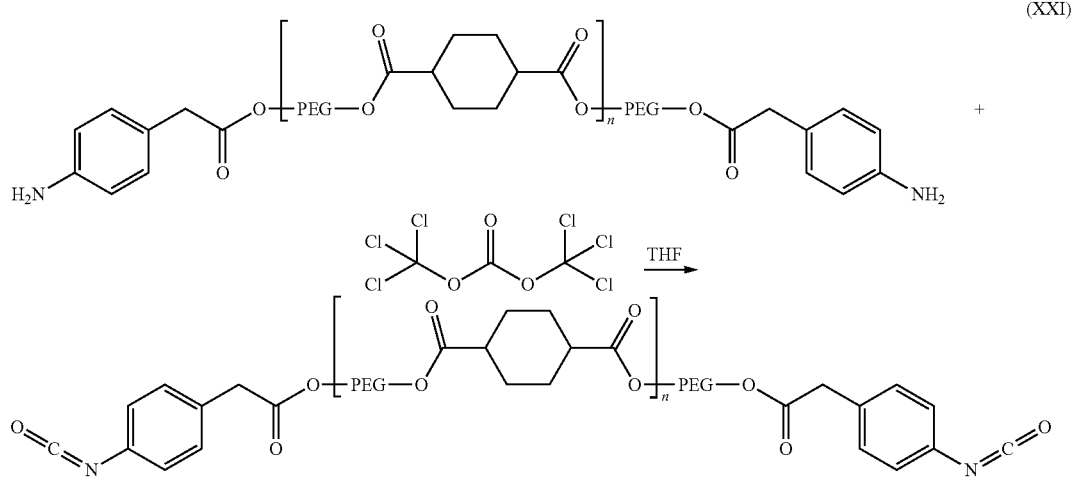

(XXI)

EXAMPLE 21

About 13.16 grams of the diisocyanate prepolymer produced in Example 20 was placed in a dry 3-neck round bottom flask and treated with about 0.09 grams of trimethylol propane. The mixture was heated at about 65° C. and kept at that temperature for about 20 hours, providing an adhesive/sealant of the present disclosure. The resulting material had an NCO content of about 2.73%, a viscosity of about 20.6 kilocentipoise and a lap shear of about 0 grams. A summary of this reaction is provided below in formula XXII.

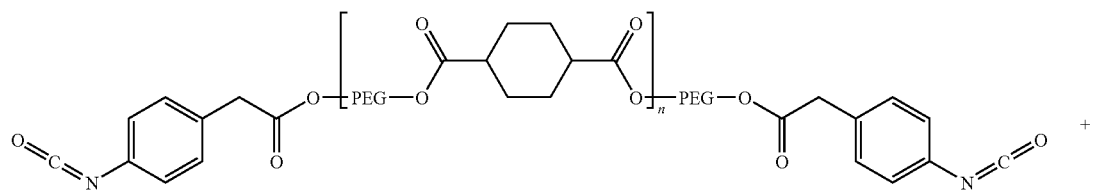

(XXII)

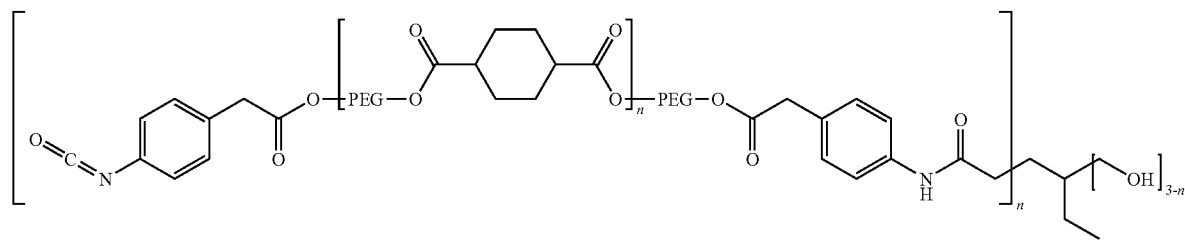

It will be understood that various modifications may be made to the embodiments disclosed herein. For example, the compositions in accordance with this disclosure can be blended with other biocompatible, bioabsorbable or non-bioabsorbable materials. As another example, optional ingredients such as dyes, fillers, medicaments or antimicrobial compounds can be added to the composition. Therefore, the above description should not be construed as limiting, but merely as exemplifications of embodiments. Those skilled in the art will envision other modifications within the scope and spirit of the claims appended hereto.

What is claimed is:

1. A biocompatible component of the formula:

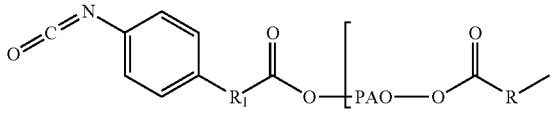

(I)

-continued wherein R is selected from the group consisting of alkyl groups, cycloalkyl groups, alkenyl groups, alkynyl groups, alkylene groups, cycloalkylene groups, alkenylene groups, alkynylene groups, aromatic groups, heteroaromatic groups, heterocyclic groups, and combinations thereof;

n can be from 1 to 5;

$R_1$ can be the same or different at each location and is selected from the group consisting of $OCH_2$, $SCH_2$, O-alkyl, S-alkyl, O-aryl, and combinations thereof; and PAO is a polyalkylene oxide having a molecular weight of from about 200 to about 4000.

2. The biocompatible component of claim 1, wherein R is selected from the group consisting of methylene, ethylene, propylene, butylene, cyclohexylene, phenylene, pyridylene, and combinations thereof.

3. The biocompatible component of claim 1, wherein the polyalkylene oxide is selected from the group consisting of polyethylene glycols, polypropylene glycols, polyethylene oxides, polypropylene oxides, polyethylene glycols with lactide linkages, polypropylene glycol-co-polyethylene oxide copolymers, polyethylene oxide/polypropylene oxide copolymers, and combinations thereof.

4. A composition comprising the biocompatible component of claim 1 in combination with a second component.

5. The composition of claim 4, wherein the second component comprises a polyol.

6. The composition of claim 5, wherein the polyol is selected from the group consisting of glycerol, trimethylol propane, hexane-1,2,6-triol, polycaprolactone triol, polyalkylene oxides, and combinations thereof.

7. The composition of claim 4, wherein the biocompatible component of claim 1 is present in an amount from about 50 to about 90 percent by weight of the composition, and the second component is present in an amount from about 10 to about 50 percent by weight of the composition.

8. A method for closing a wound comprising:
applying the composition of claim 4 to said wound; and
allowing the composition to set thereby closing said wound.

9. A method for sealing a leak in animal tissue comprising:
applying the composition of claim 4 to said leak; and
allowing the composition to set thereby sealing said leak.

10. A method for adhering a medical device to a surface of animal tissue comprising:
applying the composition of claim 4 to said device, said surface or both;
bringing the device, composition and surface into contact with each other; and
allowing the composition to set thereby adhering the device and surface to each other.

* * * * *